United States Patent
Hwang et al.

(10) Patent No.: US 7,259,869 B2
(45) Date of Patent: Aug. 21, 2007

(54) SYSTEM AND METHOD FOR PERFORMING BRIGHT FIELD AND DARK FIELD OPTICAL INSPECTION

(75) Inventors: Shiow-Hwei Hwang, Livermore, CA (US); Nat Ceglio, Pleasanton, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 198 days.

(21) Appl. No.: 11/170,578

(22) Filed: Jun. 28, 2005

(65) Prior Publication Data

US 2006/0007448 A1  Jan. 12, 2006

Related U.S. Application Data

(60) Provisional application No. 60/584,243, filed on Jun. 29, 2004.

(51) Int. Cl.
*G01B 11/02* (2006.01)

(52) U.S. Cl. .................................. 356/511

(58) Field of Classification Search .......... 356/73, 356/237.1, 237.2, 237.3, 237.4, 237.5, 511, 356/512, 513, 514
See application file for complete search history.

(56) References Cited

U.S. PATENT DOCUMENTS

| | | | |
|---|---|---|---|
| 4,340,304 A | 7/1982 | Massie | |
| 5,129,724 A | 7/1992 | Brophy et al. | |
| 5,293,538 A * | 3/1994 | Iwata et al. | 356/239.1 |
| 5,666,197 A * | 9/1997 | Guerra | 356/512 |
| 5,999,261 A | 12/1999 | Pressesky et al. | |
| 6,078,392 A | 6/2000 | Thomas et al. | |
| 6,122,046 A | 9/2000 | Almogy | |
| 6,262,818 B1 | 7/2001 | Cuche et al. | |
| 6,943,898 B2 * | 9/2005 | Libinson et al. | 356/516 |
| 2003/0227618 A1 * | 12/2003 | Some | 356/237.1 |

OTHER PUBLICATIONS

C. Koliopoulos, "Simultaneous Phase Shift Interferometer," *Advanced Optical Manufacturing and Testing II*, Proc. SPIE vol. 1531, pp. 119-127 (1991).

* cited by examiner

*Primary Examiner*—Gregory J. Toatley, Jr.
*Assistant Examiner*—Michael A. Lyons
(74) *Attorney, Agent, or Firm*—Davis Wright Tremaine LLP

(57) ABSTRACT

A system and method are disclosed for performing bright field and dark field optical inspection. In one embodiment, a system is provided for performing bright field coherent detection by means of an interferometer and dark field detection of scattered light using a single apparatus. In other embodiments, the system is operable to perform dark field detection of scattered light as well as phase measuring through phase shifting or spatial fringe analysis techniques. In yet another embodiment, an additional light source is provided for generating an illumination beam directed obliquely at the substrate to permit capture and detection of scattered light in directions near a normal direction to a surface of the substrate, and in directions away from a normal direction to a surface.

34 Claims, 7 Drawing Sheets

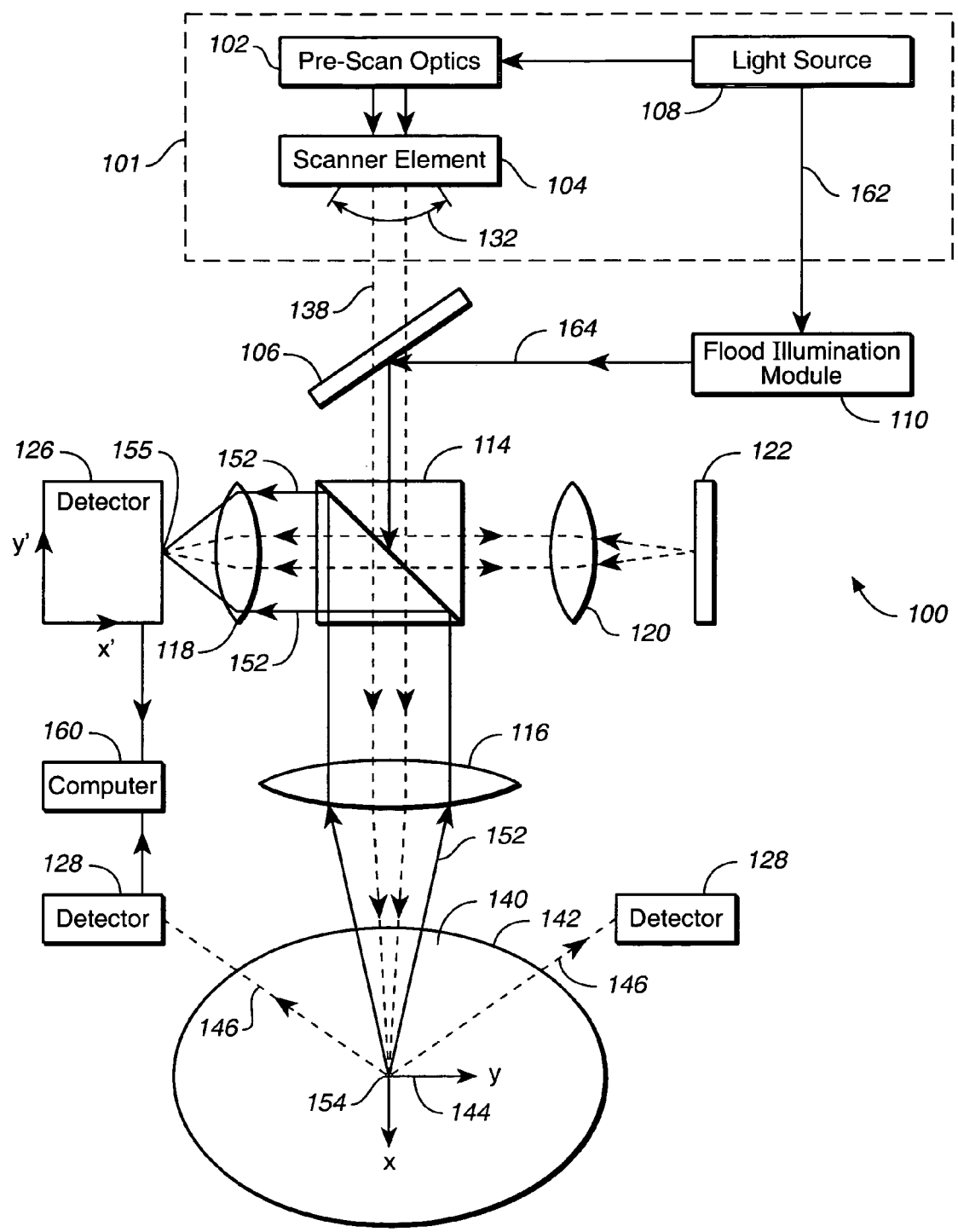
FIG._1

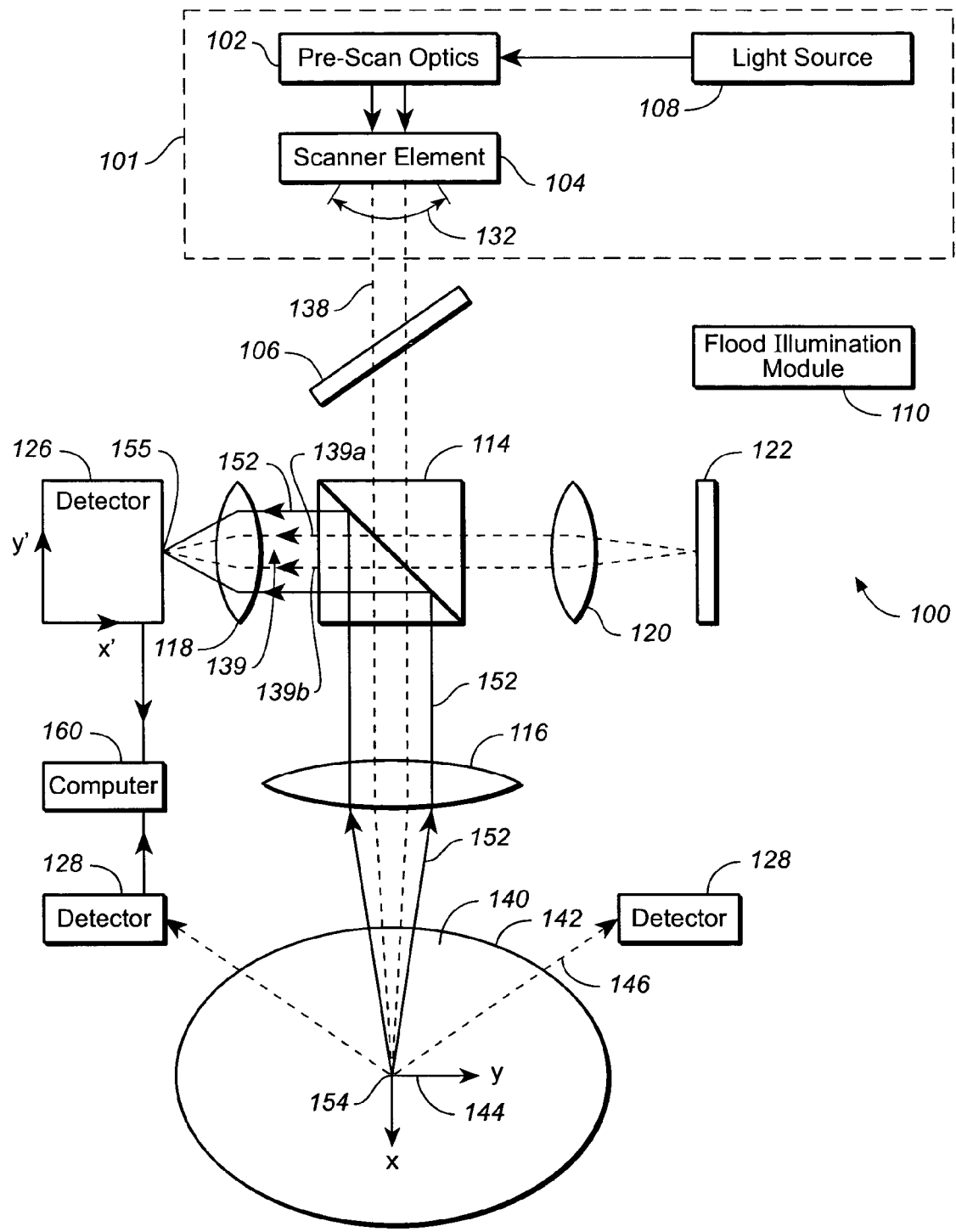
FIG._2

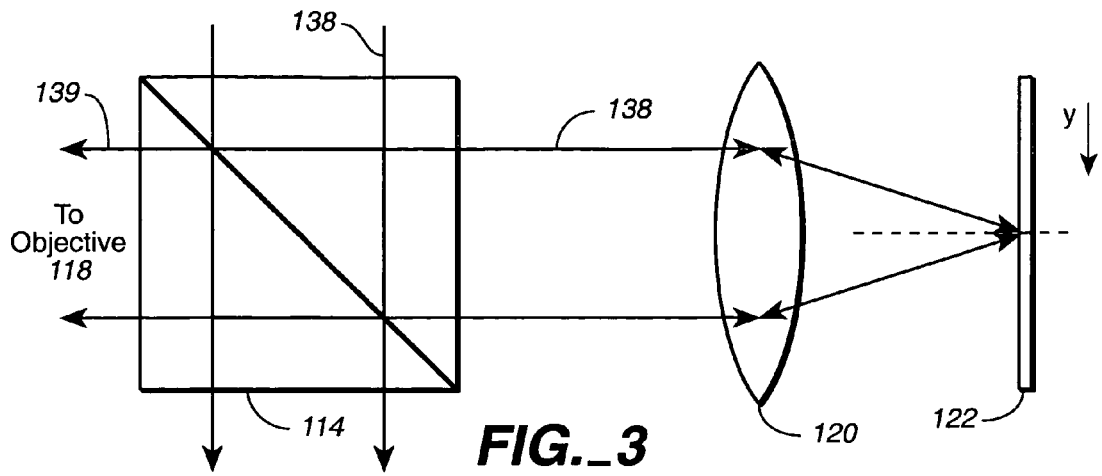
FIG._3
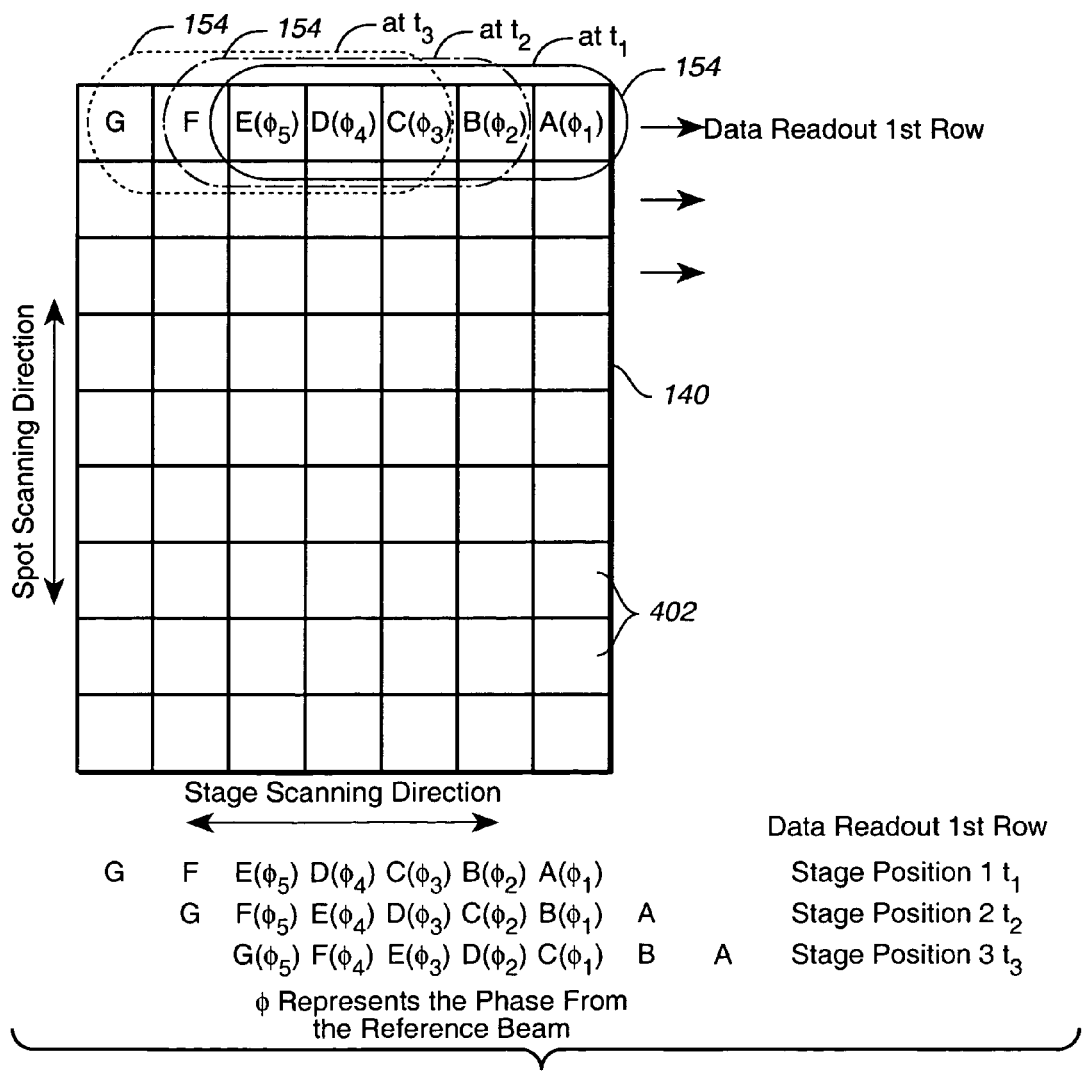
FIG._4

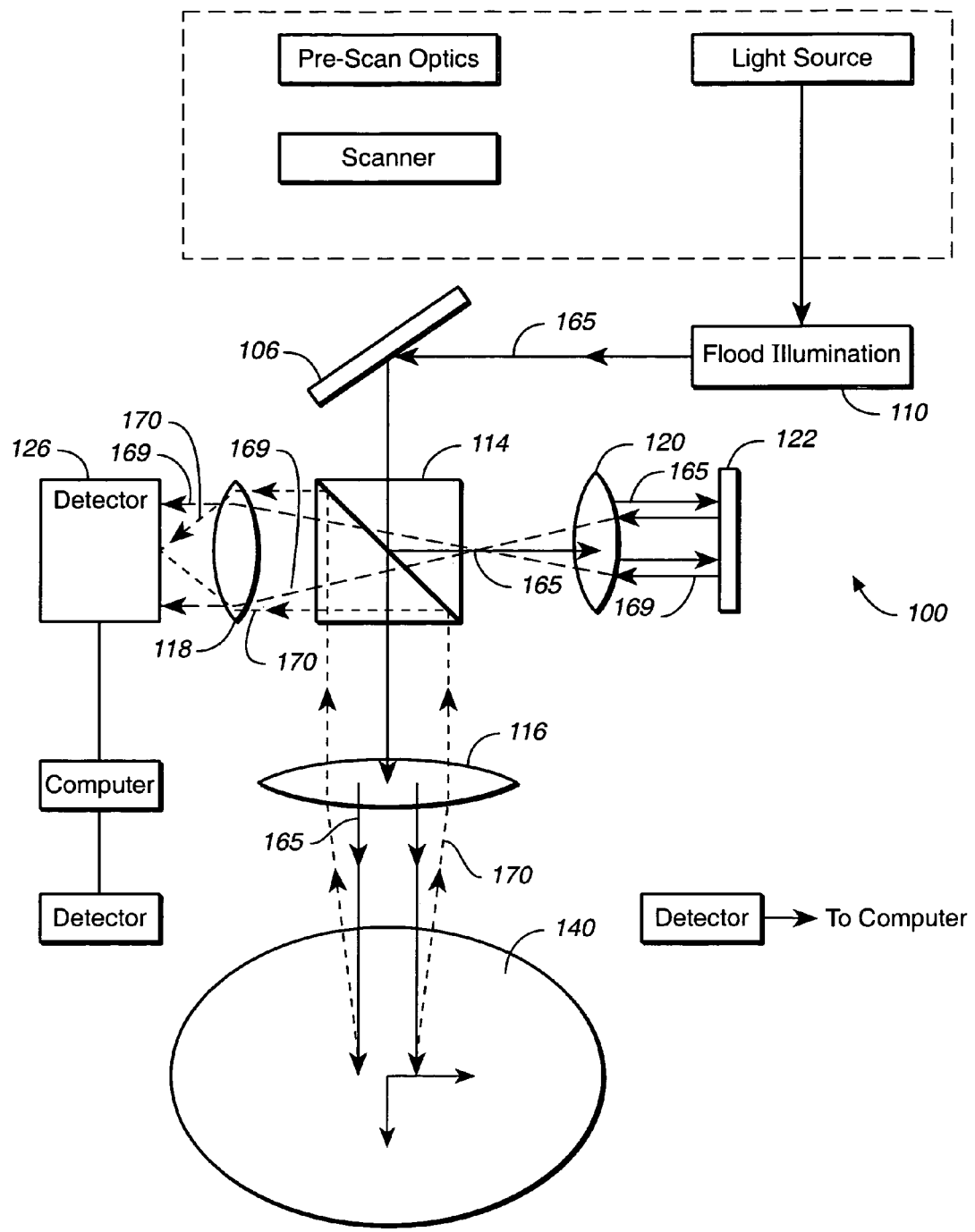
FIG._5

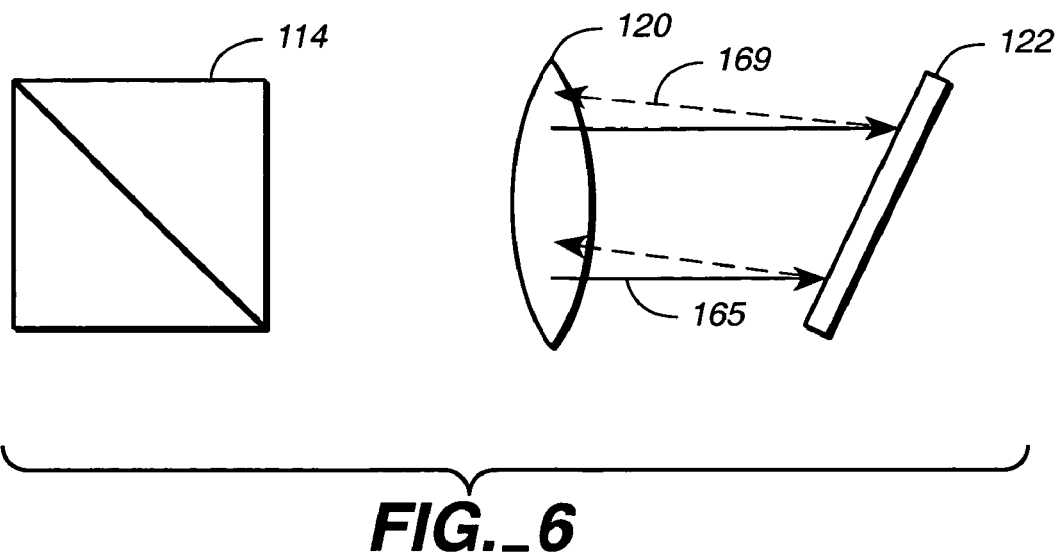
FIG._6

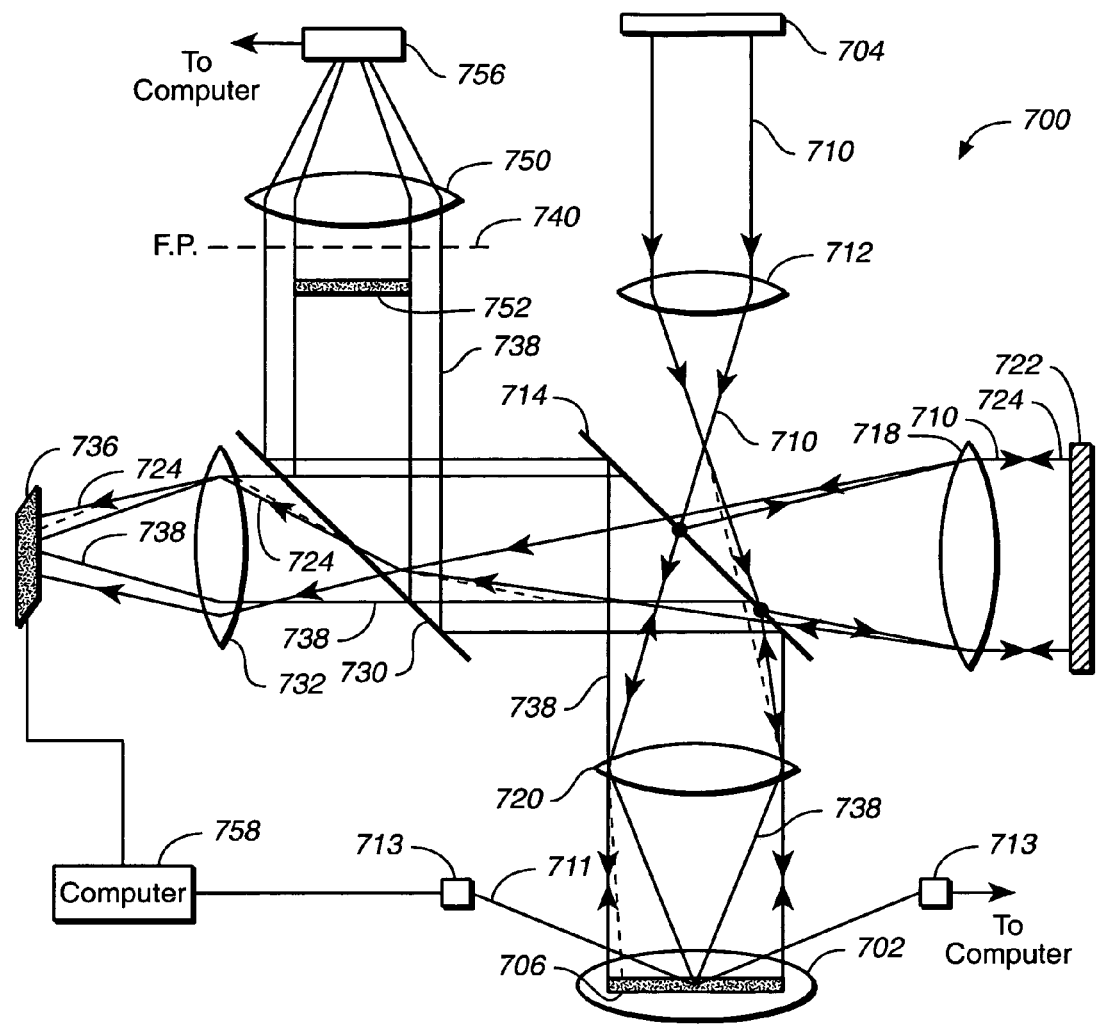
FIG._7

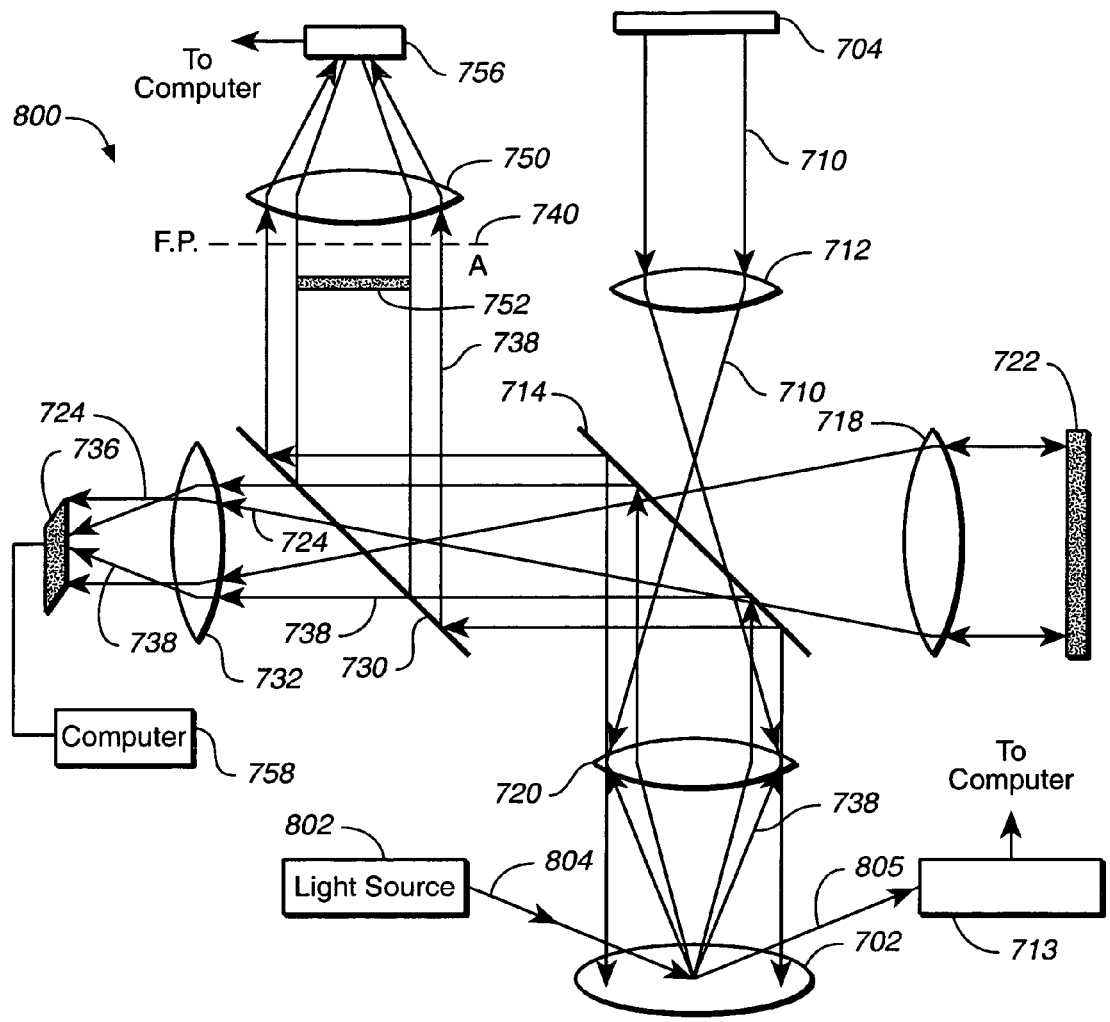
FIG._8

SYSTEM AND METHOD FOR PERFORMING BRIGHT FIELD AND DARK FIELD OPTICAL INSPECTION

CROSS REFERENCE TO RELATED APPLICATIONS

This application claims the benefit under 35 USC § 119(e) of U.S. Provisional Application No. 60/584,243, filed Jun. 29, 2004, which application is incorporated herein in its entirety.

TECHNICAL FIELD

The present system and method relate generally to systems and methods for detecting irregularities on a surface and more particularly to detecting irregularities on a silicon wafer.

BACKGROUND OF THE INVENTION

Conventionally, defect detection on semiconductor wafers can be performed with either optical or electron beam inspection. Systems and methods for inspecting semiconductor wafers for defects using optical and electron beam inspection techniques are generally well known.

Optical inspection systems frequently use either microscopic type imaging or the collection of the scattered energy. For the microscopic type of optical inspection, it may be difficult to inspect defects that generate little intensity change from the nominal structures. For example, dark defects on a dark background are typically difficult to detect due to the closeness of the change in intensity in the reflected image due to the dark defect on the dark background.

Conventional systems that collect optical images of a given substrate can be generally divided into two categories depending upon the method by which they obtain an image of a given area, namely (1) area imaging systems and (2) scanning systems. In area imaging systems, a whole area of the substrate is illuminated at once and imaging optics are used to project an image of that area or a part of it upon a detector array, such as a charge coupled device (CCD) camera. In scanning systems, however, a spot, rather than an area, is illuminated and scanned upon the substrate, and the transmitted or reflected light is measured by one or more detectors either directly or after passing through collection optics. The illumination beam may be scanned across the surface in both directions or in just one direction with mechanical motion of the substrate relative to the beam used to obtain the two-dimensional area image.

In scanning systems, illuminating light is focused upon a small spot of the substrate to be imaged and is moved across the substrate in one or two dimensions. Some of the light that is reflected or scattered from the spot is collected upon at least one detector, which is sequentially sampled. The detector's output along with the knowledge of the location of the spot location at any given time is used to reconstruct an image of the area scanned.

Area imaging systems and scanning systems have relative advantages and disadvantages. For example, one disadvantage of scanning systems is their serial, rather than parallel, nature. Hence, it typically takes longer to construct an image using a scanning system than an area imaging system. An advantage of scanning systems over area imaging systems, however, is the ability to use laser sources that have both a high brightness and a potentially narrow spectral emission range. The latter may be particularly important for UV optical systems where it is difficult to correct for spectral aberrations.

Besides the division between area illumination-based systems and laser-spot scanning-based systems, imaging systems are also divided by the direction of the illumination with respect to the collection optics. In general, if the illumination impinges, or is incident, upon the substrate from a direction such that the specularly transmitted or reflected light is collected by the imaging optics and then detected, the system is termed "bright field" ("BF"), and the detectors are known as bright field detectors. If, on the other hand, the illumination arrives from a direction which is outside the collection angle of the collection optics for the detector(s), the system is termed "dark field" ("DF").

Dark field imaging is typically used to enhance edge phenomena by collecting only the scattered light. When used for optical inspection, dark-field laser scanning systems greatly improve the signal to noise ratio for small, three-dimensional objects in a mostly flat background. Furthermore, using several dark field detectors located in different angles within the dark field may increase the chance of defect capture.

It has been found that, in some applications, defect detection can be improved by using phase detection rather than intensity based detection, because defects that create little intensity or little intensity change typically have a modest phase signal.

One system for defect detection using phase detection is disclosed in U.S. Pat. No. 6,078,392, which is incorporated herein by reference in its entirety. This patent proposes a direct-to-digital (DDH) holography approach wherein a reference beam is incident upon a reference beam mirror at a non-normal angle, and the reference beam and an object beam are focused at a focal plane of a digital recorder to form an image. This direct-to-digital holography approach, however, requires significant computational power, which may limit throughput. In addition, this approach is limited in that it does not provide for collection of scattered energy.

Additional background details are disclosed in U.S. Pat. No. 6,122,046 the disclosure of which is expressly incorporated herein by reference.

SUMMARY OF THE INVENTION

A need exists for a system and method by which advantages of various inspection techniques may be realized. In one embodiment, an inspection apparatus is provided that provides for different capabilities that include spot scanning and area imaging inspection along with coherent detection, phase measurement through spatial fringe analysis, and phase measurement through phase-shifting. Hence, embodiments of the present system and method are operable in different modes to permit inspection of a substrate using modes suited for a particular task. Obviously, one or more of such capabilities can be omitted, depending on the application desired.

One example embodiment provides for simultaneous collection of dark field diffusedly scattered light and bright field phase measurement through phase shifting. Another embodiment provides for simultaneous collection of dark field diffusedly scattered light and bright field coherent imaging.

According to another embodiment, a system is provided that, in one mode, is operable to perform spatial fringe phase measurement and, in a different mode, is operable to collect dark field scattered light.

An additional embodiment provides an inspection system that provides oblique focused illumination in one mode and flood illumination in another mode. This embodiment uses a common objective lens to collect the near-normal light scattered from the oblique illumination and to provide the bright field collection and illumination.

In an example implementation, an inspection apparatus includes a light source and a beam splitter optically coupled to the light source. A reference mirror is optically coupled to the beam splitter and an objective lens optically coupled to beam splitter and to the substrate. A bright field detector optically coupled to the beam splitter. At least a portion of an illumination beam is incident at the reference beam mirror to form a reference beam. Another portion of the illumination beam is incident upon the substrate to form an object beam, the reference beam and the object beam interfering at the bright field detector array. Dark field detectors are optically coupled to the substrate to detect scattered light from the substrate. The bright field array light detector then records an interference pattern created by the interference of the reference beam and the collected light beam.

Pursuant to one embodiment, in operation, a first laser beam is split into a reference beam and an illumination beam. The reference beam is then reflected from a reference mirror. The illumination beam is reflected from the substrate to form an object beam. The reference beam and the object beam are then incident at a detector. Obliquely scattered light from substrate is collected at dark field collectors.

BRIEF DESCRIPTION OF THE DRAWINGS

Embodiments of the present invention will be understood from the following detailed description taken in conjunction with the following drawings.

FIG. 1 is a schematic illustration of an inspection device in accordance with one embodiment of the present invention.

FIG. 2 is a schematic illustration of the inspection device of FIG. 1 showing an example mode of operation.

FIG. 3 is a schematic illustration of the reference mirror of FIG. 2.

FIG. 4 illustrates a portion of the surface inspected and data collected therefrom.

FIG. 5 is a schematic illustration of the inspection device of FIG. 1 showing another example mode of operation.

FIG. 6 is a schematic illustration of the reference mirror of FIG. 5.

FIG. 7 is a schematic illustration of an inspection device in accordance with another embodiment of the present invention.

FIG. 8 is a schematic illustration of an inspection device in accordance with yet another embodiment of the present invention.

In the drawings, like numbers are used to identify like elements.

DETAILED DESCRIPTION OF EXEMPLARY EMBODIMENTS

FIG. 1 illustrates an inspection device 100 in accordance with an example embodiment of the present invention. The inspection device 100 comprises a scanning illumination system 101, a beam splitter 106, a beam splitter 114, objectives 116, 118, 120, dark field detectors 128, a bright field detector 126, and an optional flood illumination module 10. As shown, the beam splitter 114 may comprise a cube beam splitter. The scanning illumination system 101 comprises a light source 108, pre-scan optics 102, such as a quarter-wave plate, and a scanning element 104, such as an acousto-optic deflector or rotating mirror.

As indicated by arrow 132, the scanning illumination system 101 scans an illumination beam 138 through beam splitters 106 and 114. In FIG. 1, the light beam 138 is in a centered position. The scanner element 104, however, is operable to move the beam 138 relative to a surface 140 in one direction, such as the y-direction shown in FIG. 1 while the surface 140 is moved in a perpendicular direction (i.e., the x-direction shown in FIG. 1) by a stage (not shown). To obtain a two-dimensional image of square or rectangular pixels, the mechanical velocity of the surface 140 is chosen so that the surface 140 moves by one pixel in the x-direction in the time it takes to perform a full scan in the y-direction.

The objective 116 then converts the angular scan into a focused linear scan along a scan line 144 on the surface 140 of substrate 142. The dark field detectors 128 detect scattered light 146. The dark field detectors 128 may comprise photomultipliers, whose output is sampled by data samplers (not shown). The sampling rate of the data samplers may be a function of the scanning rate. While only two dark field detectors 128 are shown in FIG. 1 it will be understood that more or fewer dark field detectors may be used.

For bright field imaging, objective 116 collects beam 152 reflected from an elliptical illumination area 154 and passes the collected light to the beam splitter 114. In one embodiment, the beam splitter 114 is a non-polarizing beam splitter. In another embodiment, the beam splitter 114 is a polarizing beam splitter and a polarizing element (not shown), such as a quarter-wave plate, is positioned between the objective 116 and the beam splitter 114.

The beam splitter 114 reflects the reflected beam 152 from the objective 116 to the detector 126 through the objective 118, which focuses the reflected light onto the bright field detector 126. In one embodiment, the bright field detector 126 comprises an array of photoelements, such as are found in a charge coupled device (CCD). Thus, as the elliptical illumination area 154 scans the across the scan line 144, a spot 155 scans along the bright field detector 126 along corresponding directions x' and y'.

Those skilled in the art will appreciate that the angular distribution of the light reflected from the elliptical illumination area 154 on surface 140 depends on the surface qualities of the surface 140. For a perfectly flat surface, all of the light will be specularly reflected back to objective 116. Substrates with three-dimensional features deflect, or scatter, a significant amount of light at low oblique collection angles. The dark-field detectors 128 detect this deflected or scattered light. In one embodiment, one or more of the dark-field detectors 128 are positioned along the spot scanning direction y.

In one embodiment, the elliptical illumination area 154 is in the shape of an ellipse with a major axis of the ellipse being oriented orthogonal to the spot scanning direction y and parallel to the stage scanning direction x. The minor axis of the ellipse is oriented orthogonal to the stage scanning direction x and parallel to the spot scanning direction y. Thus, the illumination in the direction (i.e. x-direction) orthogonal to the spot scanning direction is preferably collimated. Preferably, objective 116 focuses beam 138 so that the beam has a smaller cross-sectional dimension in the y or scanning direction and a larger cross-sectional dimension in the x or non-scanning direction. In this manner, the spot or area 154 covers a larger area of the substrate during scanning. Combination of beam scanning by element 104 and the stage allows the entire surface of the substrate to be scanned and inspected.

Flood illumination module 110 may be optically coupled to the light source 108 and receives an input beam 162 from the light source 108 and outputs a coherent, collimated reference beam 164. The reference beam 164 is reflected by the beam splitter 106, travels to the beam splitter 114, and is reflected by the beam splitter 114 to the objective 120. The objective 120 focuses the beam at the reference mirror 122. The beam is then reflected from the reference mirror 122 and is collimated through beam splitter 114 by the objective 120 at the objective 118, which focuses the reference beam at the detector 126.

A computer 160 is connected to each of the detectors 126 and 128 by conventional means and receives data collected or detected at the detectors 126 and 128. The computer 160 may then process the data received from the detectors 126 and 128.

One advantage of the system 100 of FIG. 1 is that the system 100 is operable in different modes. Hence, depending on the application, the system 100 may be used to inspect the surface 140 in a variety of different modes, examples of which are described below.

Coherent Detection Mode

As shown in FIG. 2, in one mode, the inspection device 100 is configured to provide simultaneous bright field coherent imaging and incident dark field imaging. In this mode, the flood illumination module 110 is not used. The pre-scan optics 102, in this mode, generate an illumination beam 138 that has an elliptical cross-section, such that the illuminated area 154 is elliptical, as described above. The illumination beam 138 may be formed by a cylindrical lens (not shown) disposed within the pre-scan optics 102. The illumination beam 138 illuminates the illumination area 154 on the surface 140 to generate the reflected beam 152. The objective 116 collimates the reflected beam 152. The reflected beam 152 is reflected by the beam splitter 114 and passes through the lens 118. The lens 118 focuses the reflected beam 152 at the detector 126.

As shown in FIGS. 2 and 3, the beam splitter 114, which may be 50% reflective, reflects a portion of the illumination beam 138 from element 104 toward the objective 120 and the reference mirror 122. The objective 120 receives the reflected illumination beam 138 and focuses the reflected illumination beam 138 at the reference mirror 122, such that the reflected illumination beam 138 is incident at the reference mirror 122 at a normal angle. The reference mirror 122 then reflects the illumination beam 138 through the objective 120 and the beam splitter 114 toward the objective 118 to form reference beam 139, which comprises coherent radiation. By adjusting the position of the reference mirror 122, the phase of the reference beam 139 reflected from the reference mirror 122 may be adjusted. The objective 118 then focuses the reference beam 139 at the spot 155 on the detector 126.

Accordingly, the coherent reference beam 139 and the reflected beam 152 interfere with each other at the spot 155 at detector 126. The detector 126 then records the interference pattern, or image, created by the interference of the reference beam 139 and the reflected beam 152 at the detector 126. The detector 126, in one embodiment, detects an image of the area 140 being inspected by recording data at consecutive rows of pixels at which the reflected spot 155 is incident during the scanning process.

The resultant interference pattern may then be compared with an interference pattern of a nominal or reference surface to determine the presence of significant differences between the recorded interference pattern and the nominal interference pattern. If such differences are present, they may be associated with surface features, such as defects, in the surface 140 that are not present in the nominal surface. Additional details regarding methods of coherent detection are described in U.S. Pat. No. 7,209,239 issued Apr. 24, 2007 entitled "SYSTEM AND METHOD FOR COHERENT OPTICAL INSPECTION," by Hwang et al., the disclosure of which is hereby incorporated herein by reference.

In this mode, the dark field detectors 128 detect and collect the scattered light 146 simultaneous with the detector 126 recording the interference pattern described above. The detectors 128 are positioned relative to the surface 140 to detect scattered light 146 that is scattered from the surface 140 at collection angles other than normal or near-normal. As shown in FIG. 2, two detectors 128 are shown. However, additional detectors 128 may also be employed.

The detectors 128 and the detector 126 are connected to computer 160, which receives and processes the information from the detectors 128 and the detector 126.

Phase-Shifting Mode

The system 100 is also operable, in one mode shown in FIG. 2 to include phase measuring capability through phase shifting. In this mode, the system 100 determines a phase value associated with each individual sub-divisions of the area 140. These phase values may then be compared with phase values of a reference or nominal surface to determine whether significant differences between the two sets of phase values are present. Such differences may indicate significant structural differences, such as defects, between the inspected surface 140 and the reference surface.

Pursuant to this mode of operation, the reference mirror 122 is configured such that the reference mirror 122 generates either a continuously varying phase profile or a set of discreet phase values for the reference beam 139. In some embodiments, the reference beam 139 at one edge (e.g. 139a) has a phase and at an opposite edge (e.g. 139b) has another phase, with the portions of the reference beam 139 between the two opposite edges having intermediate phases between the phases at the opposite edges.

For example, in one embodiment, the reference mirror 122 can be tilted such that the reference mirror generates a continuously varying phase profile across a cross-section of the reference beam 139. In another embodiment, an optical wedge may be employed in addition to the reference mirror 122 for altering the phase of the reference beam 139 may comprise so that the reference beam 139 comprises a continuously varying phase profile. The optical wedge can be placed between objective 120 and mirror 122. Optionally, a set of discreet phase values may be generated by using a micro-mirror array or adaptive optics so that the reference beam 139 comprises a set of different discreet phases that increase, in stepped fashion, from one edge of the reference beam 139 to an opposite edge.

The phase varying direction of the reference mirror 122, pursuant to one embodiment, is transverse (preferably perpendicular or orthogonal) to the spot scanning direction. In the embodiment of FIGS. 2 and 3, the phase varying direction is the x-direction, and the spot scanning direction (i.e., the y-direction) is perpendicular or orthogonal thereto.

FIG. 4 illustrates a portion of the surface 140 that is divided into sub-areas 402 to show data collection and readout for the phase-shifting mode. As shown, the sub-areas 402 are rectangular or square in shape and are arranged in rows and columns. The rows are aligned parallel with the stage scanning direction and the columns are aligned parallel with the spot scanning direction. The elliptical illumination area 154 is shown as being positioned in stage position 1 (at time=$t_1$), stage position 2 (at time=$t_2$), and stage position 3 (at time=$t_3$). The elliptical illumination area 154 illuminates sub-areas E, D, C, B, and A when positioned in stage position 1 (at time=$t_1$) and moves from right to left at consecutive times $t_2$ and $t_3$ in the stage scanning direction.

At the detector 126 (FIG. 2), the reflected beam 152 from the sub-areas E, D, C, B, and A is interfered with the continuously variable phase or multi-phase reference beam 139, with the light reflected from each of the sub-areas E, D, C, B, and A being interfered with light of a different phase. At time $t_1$, the portion of beam 152 reflected from sub-area E is interfered with the portion of the beam 139 having a phase $\Phi_5$, the portion of beam 152 reflected from sub-area D is interfered with the portion of the beam 139 having phase $\Phi_4$, the portion of the beam 152 reflected from sub-area C is interfered with the portion of the beam 139 having phase $\Phi_3$, the portion of the beam 152 reflected from sub-area B is interfered with the portion of the beam 139 having phase $\Phi_2$, and the portion of the beam 152 reflected from sub-area A is interfered with the portion of the beam 139 having phase $\Phi_1$. This is illustrated in FIG. 4 at stage position 1, as "E($\Phi_5$) D($\Phi_4$)C($\Phi_3$)B($\Phi_2$)A($\Phi_1$)."

In the foregoing, $\Phi$ represents the phase difference of the reference beam 139 and the coherent illumination beam 138 before beam 138 is reflected from the reference mirror 122. In one embodiment, $\Phi_5 > \Phi_4 > \Phi_3 > \Phi_2 > \Phi_1$. In another embodiment, $\Phi_5 < \Phi_4 < \Phi_3 < \Phi_2 < \Phi_1$.

Next, at time $t_2$, the beam 138 and hence the resulting elliptical illumination area 154 are positioned as shown in phantom lines in FIG. 4 and illuminates sub-areas F, E, D, C, and B. The sub-area A is not illuminated at time $t_2$. The portion of the beam 152 reflected from each of the sub-areas E, D, C, and B is interfered with the portion of the beam 139 of a different phase than at $t_1$. At time $t_2$, the portion of the beam 152 reflected from sub-area F is interfered with the portion of the beam 139 having a phase $\Phi_5$, the portion of the beam 152 reflected from sub-area E is interfered with the portion of the beam 139 having phase $\Phi_4$, the portion of the beam 152 reflected from sub-area D is interfered with the portion of the beam 139 having phase $\Phi_3$, the portion of the beam 152 reflected from sub-area C is interfered with the portion of the beam 139 having phase $\Phi_2$, and the portion of the beam 152 reflected from sub-area B is interfered with the portion of the beam 139 having phase $\Phi_1$.

At time $t_3$, the beam 138 and hence the resulting elliptical illumination area 154 are positioned as shown in phantom lines in FIG. 4 and illuminates sub-area G, F, E, D, and C. Sub-areas B and A are not illuminated at time $t_3$. At time $t_3$, the portion of the beam 152 reflected from sub-area G is interfered with the portion of the beam 139 having a phase $\Phi_5$, the portion of the beam 152 reflected from sub-area F is interfered with the portion of the beam 139 having phase $\Phi_4$, the portion of the beam 152 reflected from sub-area E is interfered with the portion of the beam 139 having phase $\Phi_3$, the portion of the beam 152 reflected from sub-area D is interfered with the portion of the beam 139 having phase $\Phi_2$, and the portion of the beam 152 reflected from sub-area C is interfered with the portion of the beam 139 having phase $\Phi_1$.

Accordingly, and as shown in FIG. 4, at each time $t_1$, $t_2$, and $t_3$, the elliptical illumination area 154 is positioned at stage positions 1, 2, and 3, respectively. At each stage position, intensity data is recorded at the detector 126 (FIG. 2) for multiple ones of the illuminated sub-areas 402. For example, for sub-area C, during times $t_1$, $t_2$, and $t_3$, the detector 126 detects and records intensity data for the sub-area C as the beam 152 is interfered with the portion of the beam 139 having phase values $\Phi_3$, $\Phi_2$, and $\Phi_1$, respectively. After recording the intensity data at the different stage positions, a phase value associated with each of the sub-areas 402 may be calculated at the computer 160 (FIG. 2) using the intensity data collected for each sub-area 402 using a different phase light for the interference at the sub-area 402.

In one embodiment, the phase values for the various sub-areas 402 may be calculated or determined in accordance with conventional phase-shifting analysis techniques, such as those described in "Simultaneous Phase Shift Interferometer," *Advanced Optical Manufacturing and Testing II*, Proc. SPIE Vol. 1531, pp. 119–127 (1991) by C. Koliopoulos, which is incorporated herein by reference.

In another embodiment, the phase values for the various sub-areas 402 may be calculated or determined in accordance with conventional coherence correlation analysis techniques.

In this mode, the dark field detectors 128 (FIG. 2) detect the scattered light 146 simultaneous with the detector 126 recording the interference pattern described above. The detectors 128 are positioned relative to the surface 140 to detect scattered light 146 that is scattered from the surface 140 at angles other than normal or near-normal. As shown in FIG. 2., two detectors 128 are shown. However, additional detectors 128 may also be employed.

Spatial Fringe Phase Measurement Mode

With reference to FIGS. 5 and 6, the system 100 can also be operated in a spatial fringe phase measurement mode. In this mode, illumination of the surface 140 is provided by the flood illumination module 110, which outputs a focused flood illumination beam 165. The reference mirror 122 is oriented such that the illumination beam 165 is incident on the reference mirror 122 at a non-normal angle after reflection by beam splitter 114. The non-normal angle may be selected according to desired fineness in the resulting spatial fringes in the collected image.

The illumination beam 165 is reflected by the beam splitter 106 and the beam splitter 114 and is then incident on the objective 120. The objective 120 collimates the illumination beam 165. The collimated illumination beam 165 then travels to the reference mirror 122 and is reflected from the reference mirror 122 at a small angle from the normal direction as reference beam 169. The reflection of beam 165 at mirror 122 as reflected beam 169 is shown more clearly in FIG. 6. The reference beam 169 then travels to the objective 120, which focuses the reference beam 169. The reference beam 169 then travels through the beam splitter 114 and is collimated by objective 118. The collimated reference beam 169 then travels to and is incident at the detector 126.

A portion of the illumination beam 165 passes from the beam splitter 106 and through the beam splitter 114 to the objective 116. The objective 116 collimates the illumination beam 165, which then illuminates an area of the surface 140, generating a reflected beam 170. The reflected beam 170 is then collimated by the objective 116 and is reflected by the beam splitter 114 toward the objective 118. The objective 118 then focuses the reflected beam 170 at the detector 126. At the detector 126, the reflected beam 170 interferes with the reference beam 169 to form an image. The image, or pattern, recorded at the detector 126 pursuant to this mode of operation includes spatial fringes that may be used as a ruler to measure the phase profile of the surface 140. The image collected by the detector 126 may be collected by scanning using conventional flash-on-the-fly or TDI (Time Delayed Integration) techniques.

Phase information regarding the surface 140 may then be determined in accordance with techniques disclosed in U.S. Pat. No. 6,078,392, the disclosure of which is expressly incorporated herein by reference in its entirety.

As shown in FIG. 5, the detectors 128 do not collect scattered light in this mode of operation, but are available to collect scattered light in other modes of operation. Additionally, the scanner element 104 does not output the beam 138 (FIG. 2) in this mode of operation.

Bright Field Detection with Dark Field Scattering

FIG. 7 illustrates a system 700 for inspecting a surface 702 in accordance with another embodiment of the present invention. The system 700 of FIG. 7 is operable to permit non-simultaneous dark field imaging and spatial fringe phase measurement using a common objective lens.

As shown, the system 700 includes an illumination source 704, such as a laser, for illuminating an area 706 on the surface 702. In the embodiment of FIG. 7, the illumination source 704 provides a flood or collimated illumination beam 710. The surface 702 may comprise a surface of a semiconductor wafer, for example.

The illumination beam 710 is focused by objective 712 and travels to a beam splitter 714. The beam splitter 714 may be, for example, 50% reflective and reflects a portion of the illumination beam 710 toward objective 718 and passes a portion of the illumination beam 710 toward objective 720. A portion of the illumination beam 710 passes through the objective 718, which collimates this portion of the illumination beam 710. The collimated illumination beam is then reflected from reference mirror 722 as reference beam 724. The reference mirror 722, in this embodiment, is oriented at a small, non-normal angle relative to the illumination beam such that the illumination beam 710 is incident at the reference mirror 722 at a non-normal angle. The non-normal angle at which the reference mirror 722 is positioned may vary.

The reference beam 724 then passes through beam splitters 714 and 730 toward objective 732. The objective 732 focuses the reference beam 724 and directs the reference beam 724 to be incident at the detector 736.

As mentioned above, the beam splitter 714 also passes a portion of the illumination beam 710 to the objective 720. The objective 710 then collimates the illumination beam to provide flood, or collimated illumination of the illuminated area 706 of the surface 702. The illuminated area 706 then reflects an object beam 738, which is captured and collimated by the objective 720 and reflected from the beam splitter 714 and through the beam splitter 730 to the objective 732. The objective 732 focuses the object beam 738 at the detector 736. Thus, the objective 732 focuses the object beam 738 and the reference beam 724 at the detector 736, which may comprise a conventional TDI detector. The object beam 738 and the reference beam 724 interfere at the detector 736. The detector 736, in turn, records an interference pattern, or image, created by the interference of the object beam 738 and the reference beam 724. Phase information from the surface 702 may be determined using the techniques disclosed in U.S. Pat. No. 6,078,392, incorporated herein by reference.

In another mode, data from scattered light may also be obtained from the surface 702 using the system 700. Spot illumination of the surface 702 may be provided by the illumination source 704, which may be configured to generate a illumination beam 710 for having an elliptical cross-section. This illumination beam 710 is then focused at a spot on the surface 702 by the objective 720. This beam may then be scanned (such as by using a scanner element) across surface of the object 702. Obliquely scattered, or diffusedly reflected, light 711 is collected at the detectors 713.

The objective 720 collects the normal or near-normal scattered or diffusedly reflected light as object beam 738 and passes the object beam 738 to the beam splitter 714, which reflects the object beam toward the beam splitter 730. The beam splitter 730 then reflects the object beam 738 toward objective 750. Fourier plane 740 associated with the object beam 738 is positioned adjacent the objective 750 and between the objective 750 and the beam splitter 730. An opaque member 752 is positioned in path of the object beam 738 between the beam splitter 730 and the objective 750.

In particular, the opaque member 752 is positioned between the Fourier plane 740 and the beam splitter 730. The opaque member 752, which may also be referred to as a "blocking aperture," is positioned centrally within the beam 738 to block the central portion of the beam from reaching and being focused by the objective 750. The light at the central portion of the beam 738 may include a high degree of interference and therefore may not be as useful as the light closer to the edges of the beam 738. Hence, the opaque member 752 blocks the light at the central portion of the beam 738 from passing to the detector 756. The opaque member 752 may comprise any of a variety of different structures that permit passage of the light outside of the central portion of the beam 738, but prevent passage of the light within the central portion of the beam 738.

The objective 750 focuses the beam 738 at the detector 756, which detects an image formed by the beam 738. The detectors 713, 736, 756 are connected to a computer 758, which receives data collected at the detectors 713, 736, 756, and processes the same.

Accordingly, the system 700 of FIG. 7 is operable to perform collection of diffusedly-scattered light, in one mode, at the detectors 756 and 713. In another mode, the system 700 is operable to perform phase measurement using interference data collected at the detector 736.

Oblique Illumination

FIG. 8 illustrates a system 800, which is identical to the system 700, except as follows. The system 800 includes an light source 802 that generates an illumination beam 804 directed at the surface 702 at an oblique angle to the surface. The light source 802 may comprise, for example, a laser. The illumination beam 804 is incident at the surface 702 at a non-normal angle. Diffused light 738 scattered from the surface 702 is collected at both the detector 713 and at the objective 720. The detector 713 is preferably placed away from the specular reflection direction of beam 804 and preferably collects oblique, low- collection angle (i.e. close to the substrate surface) scattered light 805. The objective 720 collects the normal and near-normal diffused light 738, at least a portion of which is then detected at the detector 756.

Thus, the dark field illumination from the light source 802 is not coaxial with the bright field illumination from the light source 704, which is focused at the surface 702 by the objective 720. In this embodiment, the objective 720 is operative to collect normal and near-normal scattered or diffused light 738 in one mode. In another mode, the objective 720 provides bright field illumination and bright field collection, or imaging. Moreover, similar to the system 700 of FIG. 7, the system 800 also, in one mode, is operative to perform bright field phase measurement of the surface 702.

While various embodiments of the invention have been shown and described, it will be apparent to those skilled in the art that numerous alterations may be made without departing from the inventive concepts presented herein. Thus, the invention is not to be limited except in accordance with the following claims and their equivalents. All references referred to herein are incorporated by reference herein in their entireties.

What is claimed is:

1. An inspection apparatus for inspecting a substrate, the apparatus comprising:
   a light source producing an illumination beam directed along a path to the substrate;
   an illumination objective illuminating at least a portion of the substrate with the illumination beam and collecting light originating from the illumination beam and from the substrate to form a collected light beam;
   a plurality of dark field detectors detecting light originating from the illumination beam and scattered from the substrate; and
   an interferometer comprising:
   a light detector receiving the collected light beam; and
   a reference beam mirror reflecting a portion of the illumination beam to form a reference beam, wherein the reference beam is incident at the light detector and interferes with the collected light beam at the light detector.

2. The inspection apparatus according to claim 1, wherein the illumination beam is incident upon the reference beam mirror at a normal angle of incidence.

3. The inspection apparatus according to claim 1, wherein the illumination beam is incident upon the reference beam mirror at a non-normal angle of incidence.

4. The inspection apparatus according to claim 1, wherein the reference beam has a continuously varying phase from one edge to another edge of the reference beam.

5. The inspection apparatus according to claim 1, wherein the reference beam has a set of discrete phases that increase from one edge of the reference beam to an opposite edge of the reference beam.

6. The inspection apparatus according to claim 1, wherein the light source is configured to generate an illumination beam having an elliptical shape at the substrate.

7. The inspection apparatus according to claim 1, wherein the light source is operable to provide laser-spot scanning and flood illumination to the substrate.

8. The inspection apparatus according to claim 1, wherein the reference beam comprises a coherent beam.

9. The inspection apparatus according to claim 1, wherein the illumination beam is directed at an oblique angle to the substrate.

10. The inspection apparatus according to claim 1, wherein the illumination objective collects bright field data in one mode of operation and collects dark field data in another mode of operation.

11. The inspection apparatus according to claim 1, wherein at least one of the dark field detectors is positioned to detect light scattered from the substrate in directions normal or near-normal to a surface of the substrate and at least one of the dark field detectors is positioned to detect light scattered from the substrate in a direction away from a normal direction to the surface of the substrate.

12. The inspection apparatus of claim 1, wherein at least one of the dark field detectors is positioned to detect light scattered from the substrate in directions near a normal direction to a surface of the substrate, the apparatus further comprising an opaque member positioned to block from the at least one of dark field detector light reflected in the normal direction to the surface of the substrate.

13. The inspection apparatus of claim 1, wherein the light detector comprises a charge coupled (CCD) array or a time delayed integration (TDI) CCD array.

14. The inspection apparatus of claim 1, further comprising a scanner element for moving the illumination beam relative to the substrate.

15. An inspection apparatus for inspecting a substrate, comprising:
   a light source providing a substantially coherent illumination beam;
   a beam splitter;
   a reference mirror;
   a bright field detector;
   wherein the beam splitter causes at least a portion of the illumination beam to be incident at the reference beam mirror to form a reference beam and at least a portion of the illumination beam to be incident upon the substrate to form an object beam, the reference beam and the object beam being incident and interfering at the bright field detector;
   dark field detectors detecting scattered light from the substrate.

16. The inspection apparatus of claim 15, wherein the illumination beam is incident upon the reference mirror at a normal angle.

17. The inspection apparatus of claim 16, further comprising an optical wedge altering phase of the reference beam prior to its reaching the bright field detector.

18. The inspection apparatus of claim 16, wherein the light source is configured to generate an illumination beam having an elliptical shape at the substrate.

19. The inspection apparatus of claim 16, wherein the light source provides spot illumination in one mode and flood illumination in another mode.

20. The inspection apparatus of claim 16, wherein at least one of the dark field detectors is positioned to detect light scattered from the substrate in directions normal or near-normal to a surface of the substrate and at least one of the dark field detectors is positioned to detect light scattered from the substrate in directions away from a normal direction to the surface of the substrate.

21. The inspection apparatus of claim 16, wherein the illumination beam is directed at an oblique angle to a surface of the substrate.

22. The inspection apparatus according to claim 16, wherein the reference beam has a continuously varying phase from one edge of the reference beam to another edge.

23. The inspection apparatus according to claim 16, wherein the reference beam has a set of discrete phases from one edge of the reference beam to another edge.

24. The inspection apparatus according to claim 16, wherein the objective lens collects bright field data in one mode of operation and collects dark field data in another mode of operation.

25. The inspection apparatus of claim 15, wherein the illumination beam is incident upon the reference mirror at a non-normal angle.

26. A method of inspecting a substrate, the method comprising:

splitting a first laser beam into a reference beam and an illumination beam;

reflecting the reference beam from a reference mirror;

reflecting the illumination beam from the substrate to form an object beam;

focusing the reference beam and the object beam at a detector;

collecting obliquely scattered light from substrate at dark field collectors.

27. The method of inspecting a substrate according to claim 26, wherein the reference beam comprises a light beam having a set of discreet phases from one edge of the reference beam to another edge.

28. The method of inspecting a substrate according to claim 26, wherein the reference beam comprises a light beam having a continuously varying phase from one edge of the reference beam to another edge.

29. The method of inspecting a substrate according to claim 26, wherein the reference beam is formed by reflection from the reference mirror at a normal angle.

30. The method of inspecting a substrate according to claim 26, wherein the reference beam is formed by reflection from the reference mirror at a non-normal angle.

31. The method of inspecting a substrate according to claim 26, further comprising collecting near-normal scattered light from substrate at a dark field collector.

32. The method of inspecting a substrate according to claim 26, further comprising directing a second laser beam at the substrate at an oblique angle to a surface of the substrate.

33. The method of inspecting a substrate according to claim 26, wherein the reference beam comprises a coherent light beam.

34. The method of inspecting a substrate according to claim 26 further comprising interfering the reference beam and the object beam at the detector.

* * * * *